United States Patent [19]

Ostermeier

[11] Patent Number: 4,807,463
[45] Date of Patent: Feb. 28, 1989

[54] OXYGEN MEASURING CELL

[75] Inventor: Wilhelm Ostermeier, Ratingen, Fed. Rep. of Germany

[73] Assignee: M & C Products Analysentechnik GmbH, Fed. Rep. of Germany

[21] Appl. No.: 6,721

[22] Filed: Jan. 23, 1987

[30] Foreign Application Priority Data

Oct. 3, 1986 [DE] Fed. Rep. of Germany ....... 3633750

[51] Int. Cl.$^4$ ..................... G01R 33/12; G01N 27/00
[52] U.S. Cl. ....................................... 73/27 A; 324/204
[58] Field of Search ....................... 73/27 A; 324/204

[56] References Cited

U.S. PATENT DOCUMENTS

| | | | |
|---|---|---|---|
| 2,416,344 | 2/1947 | Pauling | 73/27 A |
| 2,666,893 | 1/1954 | Munday | 73/27 A |
| 2,962,658 | 11/1960 | Munday | 324/204 |
| 3,290,921 | 12/1966 | Greene et al. | 73/27 A |
| 3,742,344 | 6/1973 | Hummel | 73/27 A |
| 3,815,081 | 6/1974 | Gast et al. | 73/27 A |
| 3,881,152 | 4/1975 | Tasaki | 73/27 A |

FOREIGN PATENT DOCUMENTS

| | | |
|---|---|---|
| 947932 | 3/1956 | Fed. Rep. of Germany . |
| 15395 | 2/1977 | Japan ..................... 73/27 A |
| 152452 | 11/1980 | Japan ..................... 324/204 |
| 137149 | 10/1981 | Japan ..................... 324/204 |
| 7214992 | 5/1973 | Netherlands ............ 73/27 A |
| 1177945 | 1/1970 | United Kingdom ...... 73/27 A |

Primary Examiner—John Chapman
Assistant Examiner—Hezron E. Williams
Attorney, Agent, or Firm—John F. A. Earley

[57] ABSTRACT

According to the present invention an oxygen measuring cell (10) is suggested comprising inlet conduit means (28) and outlet conduit means (30) for gas to be analyzed, further comprising two nitrogen-filled gas balloons (60, 62) arranged at respective ends of a dumbbell (58) which is secured, in its middle section, to a torsion part (54) arranged in transverse relationship to said dumbbell (58) for forming a torsion balance, further comprising magnet means for producing an inhomogeneous magnetic field in the region of said torsion balance, and comprising a measuring chamber (22) surrounding said torsion balance, said measuring chamber being, at least partially, of rotationally symmetric shape, said torsion part (54) extending along the longitudinal axis of said measuring chamber (22).

6 Claims, 2 Drawing Sheets

OXYGEN MEASURING CELL

The present invention relates to an oxygen measuring cell comprising an inlet conduit and an outlet conduit for gas to be analyzed, further comprizing tow nitrogen-filled gas balloons each of which is arranged at the respective end of a dumbbell which, in turn, in secured, in its middle section, to a torsion part extending in transverse relationship to said dumbbell, for forming a torsion balance, and further comprizing magnet means for producing an inhomogeneous magnetic field in the region of said torsion balance, and comprizing a measuring chamber surrounding said torsion balance.

Such an oxygen measuring cell utilizes the high value of the magnetic susceptibility of oxygen. If a gas containing oxygen enters the cell the oxygen tends to reach the region of highest magnetic flux and thus tries to press the diamagnetic gas balloons to the side. The torsion balance consisting of torsion part and dumbbell is displaced, and the torque produced in this manner is directly proportional to the oxygen content of the gas being analyzed.

The torque is usually measured by noting the displacement of a light beam which is introduced into the measuring chamber from the outside, impinges on a small mirror arranged at the middle section of the dumbbell, and which is reflected back to the outside. It is further known to compensate the torque induced by the oxygen content by the magnetic field produced by a conducting loop which is suitably arranged in the measuring chamber and through which an electric current is passed. At a certain current intensity the torque produced by the oxygen content of the gas being analysed is exactly compensated and, therefore, the mirror returns to its zero position. Therefore, the current or the voltage applied to the loop, respectively, is a measure of the torque produced by the oxygen content of the gas being analyzed. The zero position of the mirror may easily by controlled by controlling the reflected beam of light, for example by means of a photo cell or a differential photo cell.

The current meter may be gauged directly, in this manner, in percent oxygen.

Usually known oxygen measuring cells comprize a body of metal sheets arranged in perpendicular relationship to each other, the sheet metal body being open at one side and having a glass plate for covering the opening; the light beam can traverse the glass plate. In order to have a gas-tight cell, in the prior art cells the metal sheets and the glass plate are bonded together with an adhesive material. If the gas to be analyzed has an elevated temperature the adhesive starts to gas out, thus emitting further gas which introduces an error into the measurement. The light beam is refracted during its passage through the glass plate, once on entering and again during its return thus leading to errors and/or adjustment troubles.

Furthermore, prior art oxygen measuring cells have a relatively large dead volume yielding a relatively long response time, in the order of 8 seconds or more. If such an oxygen measuring cell is employed with respect to explosion hazards such a long response time might be too long for starting measures against the explosion hazard.

In addition, the gas to be analyzed is led, in prior art oxygen measuring cells, into the measuring cells via multiple reversions and exits in a similar manner. This leads to turbulences at higher flow rates which interfere with the mechanically extremely sensitive torsion balance, and for this reason only small flow rates are acceptible, that is flow rates where no turbulences occur, in the order of magnitude of 1 to 15 liters per second.

In prior art measuring cells the torsion part is secured to the housing. As the torsion part is very thin and may hardly be stressed mechanically, mounting of the torsion part in prior art measuring cells is very difficult, and frequently a torsion part is damaged during the mounting procedure. This leads to a high reject rate during manufacturing. Furthermore, with prior art structures there is virtually no possibility to replace a torsion part which has been unduly stressed. In such a case the entire oxygen measuring cell has to be replaced, thus leading to high operation costs for oxygen analyzers.

It is therefore an object of the invention to advance prior art oxygen measuring cells and to provide an oxygen measuring cell where the above-indicated problems are reduced or do not occur at all.

The present invention is based on the finding that, previously, the flow conditions in an oxygen measuring cell have been neglected and dead volumes have been admitted which were too large, as no optimization in this respect has taken place.

According to the present invention the objects are reached by providing an oxygen measuring cell with an inlet conduit and an outlet conduit for gas to be analyzed, with two nitrogen-filled gas balloons arranged at the ends of a dumbbell which is secured, in its middle section, to a torsion part extending in transverse relation thereto for forming a torsion balance, further comprizing magnets for producing an inhomogeneous magnetic field in the region of the torsion balance, and comprizing a measuring chamber surrounding the torsion balance, the measuring chamber being at least partially rotationally symmetric, and the torsion part extending along the longitudinal axis of the measuring chamber.

The arrangement of the torsion part along the axis of rotational symmetry of the measuring chamber has distinct advantages. First, the refraction of the light beam is clearly reduced or avoided alltogether, because the light beam no longer has to pass a plane parallel plate twice at an oblique angle but rather passes, exactly radially, the measuring chamber wall which is curved, in rotationally symmetric fashion, around the longitudinal axis. Furthermore, the dead volumes are clearly reduced in such a rotationally symmetric measuring chamber. The inner diameter of the measuring chamber which is at least partially rotationally symmetric must only be as large as the longitudinal extension of the oscillating dumbbell. In this manner the response time of the cell according to the present invention is considerably improved and is in the order of magnitude of 3 seconds or less.

According to another preferred embodiment of the oxygen measuring cell according to the present invention the torsion part is a torsion wire or a torsion tape, preferably made of a platinum-rhodium alloy. Such a torsion wire or tape may be manufactured with constant properties and is resistant to numerous gases and gas mixtures, in particular to aggressive gases. This is important for the spring rate properties which should not change under the influence of the gas, thus leading to measuring errors.

Preferably the measuring chamber is of cylindrical shape and the torsion part extends along the longitudinal axis of the cylinder. Hollow cylinders for receiving the torsion part are available in a plurality of standardized dimensions, wall thicknesses, and so on, thus reducing manufacturing costs. The material of the measuring chamber is advantageously chosen with respect to the gas or gas mixture to be analyzed in order to have a measuring chamber made from a material which is resistant with respect to this gas or gas mixture. In particular, the material should not gas out even at high temperatures which might occur for shorter or longer periods even with gases which are usually cooler, as otherwise additional gas would be released in the measuring chamber and would induce an error.

According to a particular advantageous embodiment of the invention the measuring chamber is made of glass, of hard glass, or of silica glass. Such glasses have found numerous applications in analytical chemistry and physics and may be adapted to a plurality of applications. As such glasses are transparent a separate plate for transmitting the light beam to the mirror is not necessary, thus leading to an additional cost reduction and avoiding refraction problems.

With such an embodiment a separate mounting of the torsion part may be provided in an advantageous manner. It is particularly advantageous if, in another embodiment of the invention, a holding means for the torsion part is provided which is detachable from the measuring chamber. In this manner the torsion part may first be separately mounted to the holding means and can be tested. Of course even the entire torsion balance consisting of the torsion part, the dumbbell with the glass balloons, and the mirror, may be fastened to the holding means and be tested. The arrangement consisting of torsion balance and holding means is subsequently mounted in the measuring chamber. Firstly, the mounting is decisively simplified. Furthermore, for the first time a chance for a repair is provided, because the holding means with the torsion balance may easily be detached from the measuring chamber if a part of the torsion balance has been damaged, and a new holding means with a premounted torsion balance may be inserted.

A particular simple embodiment of the holding means according to the present invention comprises a longish plate which is, at least partially, adapted to the shape of the measuring chamber and comprizes two holding arms suspending the torsion part therebetween. The holding arms are preferably made of a slight resiliant material in order to exert a constant spring action on the torsion part. The material of the plate and the holding arms should be resistant to corrosion and ageing in a similar manner as the material of the torsion part. It is also feasible, however, to fasten the holding arms (without a plate) directly to the measuring chamber wall.

In order to avoid turbulences of the gas flow to be analyzed, according to another preferred embodiment of the invention the inlet conduit and/or the outlet conduit for the gas to be analyzed is arranged such that it runs in the direction of the longitudinal axis of the measuring chamber, at least in those sections adjacent to the measuring chamber. Therefore, the gas flows lineally into the measuring chamber in the direction of the torsion part and leaves the chamber in the same direction; in particular the gas flow is not deflected in the measuring chamber. In this manner turbulences are avoided and the admissible throughput is considerably enlarged, up to approximately 50 liters per second as compared to the prior art mentioned above.

For providing an even, non-turbulent gas flow there is a further advantage if the connecting part in between the gas inlet or the gas outlet and the measuring chamber, respectively, is optimized with respect to a free, undisturbed gas flow. For this purpose either smooth transitions with constant cross sections or smoothly tapered transitions in between these sections are provided.

It has been found that a common source for damaging prior art measuring cells were particles of solid matter contained in the gas flow to be analysed, which could damage the extremely delicate torsion balance. In order to ensure a trouble free operation also in this respect it is suggested, according to another preferred embodiment of the present invention, to provide a sieve in the gas inlet conduit or in the region of the inlet side of the measuring chamber, the sieve being preferably made of sintered metal, the sieve being resistant to the usual gases to be analyzed and being dimensionally stable during temperature changes.

In a preferred embodiment of an open housing a bottom part and a cover part are separated by spacer means or spacer bushings which may easier be manufactured with greater precision than rectangular side walls.

The invention is subsequently explained in more detail in connection with a preferred embodiment and associated drawings showing further advantages and features.

In the figures.

Figure 1:
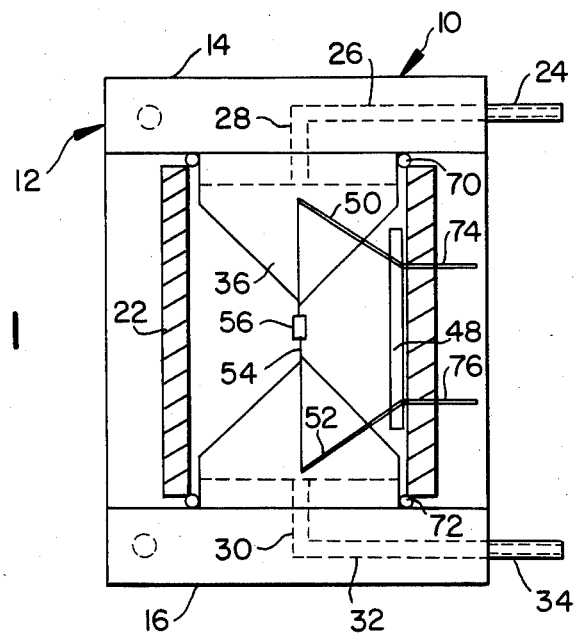
FIG. 1 is a side view in a vertical cross section of a measuring chamber and housing according to the present invention.
Figure 2:
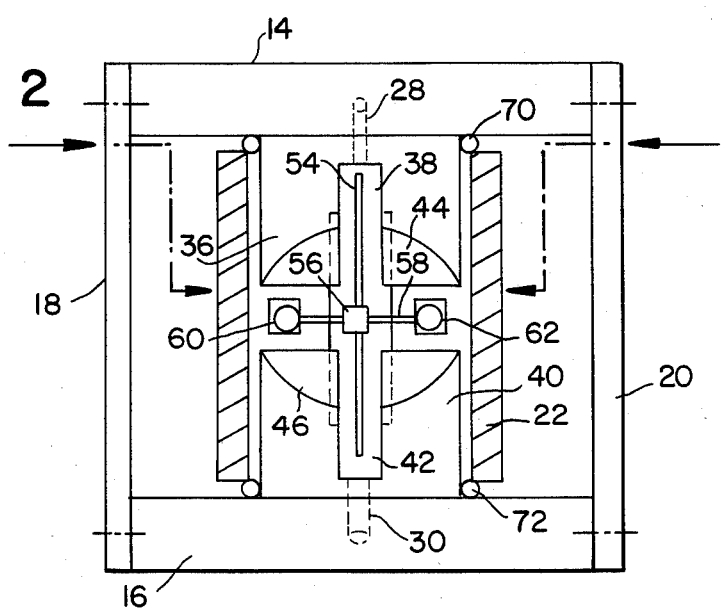
FIG. 2 is a front view in a vertical cross section of a measuring chamber and housing according to the present invention.
Figure 3:
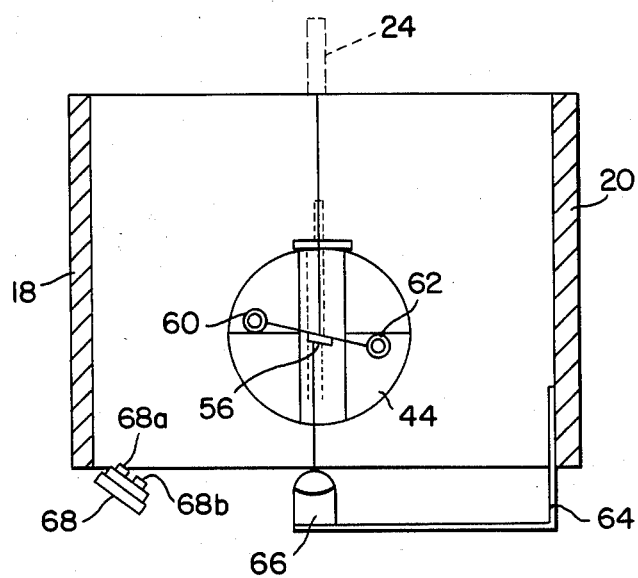
FIG. 3 is a top view on a horizontal cross section along lines AB of FIG. 2 of an oxygen measuring cell according to the present invention.

The measuring cell 10 shown in FIGS. 1, 2, and 3 comprises a housing 12 with a cover 14, a bottom 16, and two side walls 18 and 20, respectively. The housing is open at the front and at the back.

Gas to be analyzed is introduced via a gas inlet pipe 24 arranged at the cover 14, and the pipe 24 continues, inside of cover 14, to an inlet pipe 26 which runs into a gas inlet 28. Opposed to gas inlet 28 a gas outlet 30 is arranged in bottom 16 of housing 12, the outlet running into an outlet pipe 32 which, in turn, is connected to a gas outlet pipe 34.

Gas inlet 28 and gas outlet 30, respectively, extend in concentric alignment to and along the longitudinal axis of a measuring chamber 22. The measuring chamber 22 is a hollow glass cylinder with open ends.

In the measuring chamber 22 an upper pole piece 36 comprising a recess 38 and an oppositely arranged lower pole piece 40 comprising a recess 42 are provided, the recess 42 being in opposed relationship to recess 38. Upper pole piece 36 has an inclined upper surface 44 and correspondingly lower pole piece 40 has a lower inclined surface 46. Inclined surfaces 44, 46 are in mutually opposed relationship. In between the end edges of inclined surfaces 44, 46 an inhomogeneous magnetic field is produced under the influence of magnets arranged at the outside acting upon the pole pieces which are made of soft iron.

At a section of the inner wall or measuring chamber 22 a holding plate 48 is arranged. From the holding plate an upper support bracket 50 and a lower support bracket 52, respectively, project into the inside of measuring chamber 22. Support brackets 50, 52 extend from holding plate 48 to the central longitudinal axis of measuring chamber 22. Between the ends of support brackets 50, 52 a torsion tape 54 made of a platinumrhodium alloy is tensionally arranged.

As shown in particular in FIG. 2, in the middle section of torsion tape 54 a dumbbell bar 58 is secured in its middle section, the dumbbell bar bearing gas balloons 60, 62, respectively, at either end. Gas balloons 60, 62 are filled with nitrogen and hermetically sealed.

In order to reduce corrosion the pole pieces are nickel plated. In case the pole pieces would corrode anyhow, which might impede the movement in the narrow air gap, the pole pieces could easily be replaced.

Furthermore, at the section connecting dumbbell bar 58 and torsion tape 54 a mirror 56 is arranged, the function of which will be subsequently explained in more detail in connection with FIG. 3.

Instead of using, as in the prior art, a glass plate with an evaporated aluminum layer as a mirror, in the present invention a platinum surface is evaporated onto a glass plate. This leads to a high corrosion resistance as well as to a better adjustment of the (better) corrosion properties of the different components.

The glass cylinder 22 forming the measuring chamber is sealed, as shown in particular in FIGS. 1 and 2, at its one end against cover 14 of housing 12 via an O-ring 70 made of Viton and, at its other opposed end, against bottom 16 of housing via an O-ring 72 made of Viton. Of course other seals might be employed, for example made of natural or synthetic rubber, of silicon rubber, of PTFE, of "KARLREZ" (Du Pont Corp.) and so on. Also, seals made of soft metals, for example made of iridium tape, might eventually be used. The choice of a particular seal is essentially determined from the properties and the temperature of the gases which are to be analyzed.

Additional measures can be taken for sealing measuring chamber 22 with respect to cover 14 and bottom 16. For example, in the cover 14 or bottom 16, respectively, a groove may be provided which particularly receives O-ring 70 or 72, respectively, such that a gas-tight connection is provided between measuring chamber 22 and cover 14 or bottom 16, respectively. In the end sections of measuring chamber 22 and/or in the cover 14 and/or in the bottom 16 further or additional inclined surfaces may be provided for improving the sealing action.

The arrangement of the measuring cell according to the present invention and its function is displayed particularly distinctly in the top view on a horizontal cross section of FIG. 3. The dumbbell of the torsion balance with the two gas balloons 60, 62 at either end carries the mirror 56 in its middle section, and a light beam emitted by a lamp 66 disposed at a holder 64 attached to side wall 20 of housing 12 impinges onto the mirror. The light beam from lamp 66 is reflected at the mirror 56 and is sent back, in a definite angle determined by the torsion of torsion tape 54, to the outside. The reflected light beam reaches the outside through wall 22 and can be registered at the outside by means of a photo cell 68. The zero position of mirror 56 may easily be adjusted by turning the galss cylinder 22.

Photo cell 68 is constructed, as indicated in figure 3, as a differential photo cell comprising, therefore, a (left) photo cell 68a and a (right) photo cell 68b. Photo cell 68 is arranged such that in the position of equilibrium of the torsion balance, that is when no torque acts upon the torsion balance, the reflected light beam is right in the middle between the photo cells 68a and 68b. Starting from this zero position the torsion balance will be deflected with a certain torque being proportional to the oxygen concentration when a gas containing oxygen enters the measuring chamber according to the present invention. Therefore, the mirror attached to the dumbbell bar 58 of te torsion balance moves, and this lead to a deflection of the light beam reflected by the mirror 56 and the light beam now impinges not in the middle between the photo cells 68a, 68a, but next to that position, for example directly on photo cell 68a. In this case, photo cell 68a emits a control signal which increases the voltage impressed on the compensation loop mentioned above, thus increasing the current through the loop, whereby a magnetic field intensity is produced which counteracts the torque produced by the oxygen concentration. The voltage is increased until the photo cell 68a is no longer hit by the light beam and until the light beam has returned to the position in between photo cells 68a and 68b.

This balance method with a torque compensation is particularly advantageous because in this manner it is assured that the torsion tape is kept in its linear range and therefore the measurement is strictly linear.

In this case, the compensation voltage at the wire loop is a direct measure for the oxygen concentration. Corresponding considerations are valid for a deflection of the light beam in the opposite direction, for example from the zero position to photo cell 68b.

Current supply to the wire loop is provided via pins 74, 76 traversing holding plate 48 and the wall of the measuring chamber 22 and leading to the wire loop which extends as shown in the wire sections adjacently surrounding the gas balloons 60, 62 which wire sections are bent rectangularly, as shown in FIG. 2.

I claim:

1. A device for measuring oxygen comprising in combination: hollow chamber means formed to be substantially cylindrical in shape with a central longitudinal axis and having a top end aperture and a lower end aperture and fabricated of transparent material top end means formed to pass magnetic flux and having a base section and an inclined section, said base section formed to substantially match said top end aperture and being inserted, said inclined section first, into said hollow chamber means to substantially form a seal between said top end means and said top end aperture, said inclined section of said top end means having at least first and second beveled side sections which start at said base section of said top end means and are inclined toward each other so as to end in a ridge formed between said last mentioned beveled side sections; lower end means formed to pass magnetic flux and having a base section and an inclined section, said base section formed to substantially match said lower end aperture and being inserted, said inclined section first, into said hollow chamber means to substantially form a seal between said lower end means and said lower end aperture, said inclined section of said lower end means having at least first and second beveled side sections which start at said base section of said lower end means and are inclined toward each other so as to end in a ridge formed between said last mentioned beveled side sections; said top end means disposed with respect to said lower end means in said hollow chamber to define a free space section of said hollow chamber means so that magnetic flux passing through said first and second beveled side sections of said top end means into said first and second beveled side sections of said lower end means creates an inharmonious field of magnetic flux between said top end means and said lower end means; dumbbell shaped means with gas filled retainers on either end and including mounting means which are disposed to enable said dumbbell shaped means to partially rotate in said free space around said central longitudinal axis of said hollow chamber; first and second gas conduit means formed respectively in said top end means and in said lower end means to enable gases containing oxygen to pass through said top end means, through said free space, across said gas filled retainers to create a torque by said dumbbell shaped means, commensurate with the quantity of oxygen present in said gases passing through said hollow chamber.

2. A device for measuring oxygen according to claim 1 wherein said mounting means is removably attached to a side wall of said hollow chamber means.

3. A device for measuring oxygen according to claim 1 wherein said dumbbell shaped means includes a light reflecting means which reflects light through walls of said hollow chamber means to indicate the torque created by said dumbbell shaped means.

4. A device for measuring oxygen according to claim 1 wherein in said top end means and said lower end means each has a slot formed therein and wherein said mounting means fits into said respected slots.

5. A device for measuring oxygen according to claim 1 wherein there is further included first and second O-rings with said first O-ring fitted between said top end means and said hollow chamber means and with said second O-ring fitted between said lower end means and said hollow chamber means.

6. A device for measuring oxygen comprising in combination: hollow chamber means formed to be substantially cylindrical in shape with a central longitudinal axis and having a top end aperture and a lower end aperture and fabricated of transparent material; top end means formed to pass magnetic flux, said top end means having a portion formed to substantially match said top end aperture and being inserted into said hollow chamber means to substantially form a seal between said top end means and said top end aperture; lower end means formed to pass magnetic flux, said lower end means having a portion formed to substantially match said lower end aperture and being inserted into said hollow chamber means to substantially form a seal between said lower end means and said lower end aperture; said top means disposed with respect to said lower end means in said hollow chamber to define a free space section of said hollow chamber means so that magnetic flux passing through said top end means into said lower end means creates an inharmonious field of magnetic flux between said top end means and said lower end means; dumbbell shaped means with gas filled retainer on either end and including mounting means which are disposed to enable dumbbell shaped means to partially rotate in said free space around said central longitudinal axis of said hollow chamber; first and second gas conduit means formed respectively in said top end means and in said lower end means to enable gases containing oxygen to pass through said top end means, through said free space, across said gas filled retainers to create a torque by said dumbbell shaped means, commensurate with the quantity of oxygen present in said gases passing through said hollow chamber.

* * * * *